United States Patent
O'Brien et al.

(10) Patent No.: US 9,427,698 B2
(45) Date of Patent: Aug. 30, 2016

(54) AMINO-SILOXANE COMPOSITION AND METHODS OF USING THE SAME

(71) Applicant: General Electric Company, Schenectady, NY (US)

(72) Inventors: Michael Joseph O'Brien, Town of Halfmoon, NY (US); Rachel Lizabeth Farnum, Rensselaer, NY (US); Robert James Perry, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 216 days.

(21) Appl. No.: 14/051,594

(22) Filed: Oct. 11, 2013

(65) Prior Publication Data
US 2015/0104366 A1    Apr. 16, 2015

(51) Int. Cl.
| | | |
|---|---|---|
| B01D 53/14 | (2006.01) | |
| C10K 1/00 | (2006.01) | |
| C10K 1/12 | (2006.01) | |
| C10K 1/14 | (2006.01) | |
| C10K 1/16 | (2006.01) | |

(52) U.S. Cl.
CPC ....... B01D 53/1493 (2013.01); B01D 53/1475 (2013.01); C10K 1/005 (2013.01); C10K 1/128 (2013.01); *B01D 2252/2041* (2013.01); *B01D 2252/2053* (2013.01); *B01D 2252/20415* (2013.01); *B01D 2252/20426* (2013.01); *B01D 2252/20431* (2013.01); *B01D 2252/20452* (2013.01); *B01D 2258/0283* (2013.01); *Y02C 10/06* (2013.01); *Y02P 20/152* (2015.11)

(58) Field of Classification Search
CPC .......... B01D 53/1475; B01D 15/1493; B01D 2252/2041; B01D 2252/2053; B01D 2252/20415; B01D 2252/20426; B01D 2252/20431; B01D 2252/20452; B01D 2258/0283; C10K 1/005; C10K 1/16; C10K 1/128; C10K 1/143
See application file for complete search history.

(56) References Cited

U.S. PATENT DOCUMENTS

| | | |
|---|---|---|
| 7,998,714 B2 | 8/2011 | Gellett et al. |
| 8,030,509 B2 | 10/2011 | Perry et al. |
| 2006/0165574 A1 | 7/2006 | Sayari |
| 2010/0154431 A1 | 6/2010 | Genovese et al. |
| 2010/0154639 A1 | 6/2010 | Perry et al. |
| 2012/0171095 A1 | 7/2012 | O'Brien et al. |

FOREIGN PATENT DOCUMENTS

| | | |
|---|---|---|
| EP | 0674936 B1 | 10/1995 |
| WO | 2012138755 A1 | 10/2012 |

OTHER PUBLICATIONS

"2000/01 Catalog of Organics and Fine Chemicals." Acros Organics, (c) 2001 (excerpt).*
"Wabash River Coal Gasification Repowering Project: A DOE Assessment." U.S. Dept. of Energy (DOE/NETL-2002/1164, Jan. 2002).*
Perry et al., "Aminosilicone Solvents for CO2 Capture", ChemSusChem, Aug. 23, 2010, vol. 3, Issue 8, pp. 919-930.
Perry et al., "Novel High Capacity Oligomers for Low Cost CO2 Capture", Technical report, Dec. 2010, DOE, DE-NT0005310, 213 Pages.
Perry et al., "Amino Disiloxanes for CO2 Capture", Energy & Fuels, Mar. 10, 2011, vol. 25, Issue 4, pp. 1906-1918.
Perry et al., "CO2 Capture Using Solutions of Alkanolamines and Aminosilicones", Energy & Fuels, Mar. 2, 2012, vol. 26 Issue 4, pp. 2512-2517.
Perry et al., "CO2 Capture Using Phase-Changing Sorbents", Energy & Fuels, Mar. 20, 2012, vol. 26, Issue 4, pp. 2528-2538.

* cited by examiner

*Primary Examiner* — Daniel Berns
(74) *Attorney, Agent, or Firm* — Francis T. Coppa

(57) ABSTRACT

An amino-siloxane composition is presented. The amino-siloxane composition includes structure (I):

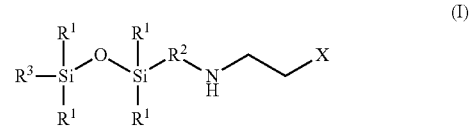

wherein $R^1$ is independently at each occurrence a $C_1$-$C_5$ aliphatic radical; $R^2$ is a $C_3$-$C_4$ aliphatic radical; $R^3$ is a $C_1$-$C_5$ aliphatic radical or $R^4$, wherein $R^4$ comprises structure (II):

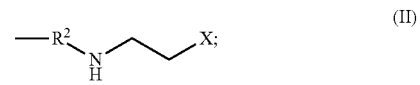

and X is an electron donating group. Methods of reducing an amount of carbon dioxide in a process stream using the amino-siloxane composition are also presented.

8 Claims, No Drawings

AMINO-SILOXANE COMPOSITION AND METHODS OF USING THE SAME

STATEMENT REGARDING FEDERALLY SPONSORED RESEARCH & DEVELOPMENT

This invention was made with Government support under grant number DE-AR-0000084 awarded by the Department of Energy. The Government has certain rights in the invention.

BACKGROUND

Power generating processes that are based on combustion of carbon containing fuel typically produce carbon dioxide ($CO_2$) as a byproduct. It may be desirable to capture or otherwise separate the $CO_2$ from the gas mixture to prevent the release of $CO_2$ into the environment, and/or to utilize $CO_2$ in the power generation process or in other processes.

However, typical $CO_2$ capture processes, such as, for example, an aqueous amine-based process (MEA-based process), may have limitations, for example, the process can sometimes result in sharp increases in the viscosity of the liquid absorbent, which can decrease the mass transfer of $CO_2$ into the sorbent. To avoid this problem, the concentration of amines in the absorbent stream may be maintained at low levels (using carrier solvents), which may greatly reduce absorbing capacity, as compared to the theoretical capacity of the neat absorbent. Moreover, energy consumption in the amine process may be high, due in large part to the need for heating and evaporation of the carrier solvent (for example, water).

There are many properties that desirably would be exhibited, or enhanced, in any $CO_2$ capture technology and absorbents contemplated to be a feasible alternative to the currently utilized MEA-based processes. For example, any such absorbent would desirably exhibit a high net $CO_2$ capacity, and could provide lower capital and operating costs (less material volume required to heat and cool, therefore less energy required). A lower heat of reaction would mean that less energy would be required to release the $CO_2$ from the material. Absorbents with lower viscosities would provide improved mass transfer, reducing the size of equipment needed, as well as a reduction in the cost of energy to run it.

Thus, there is a need for $CO_2$-capture absorbents and methods of use thereof that optimize as many of the above desired properties as possible. Further, there is a need for $CO_2$-capture absorbents and methods of use thereof such that the absorbents have low viscosity and low heat of reaction.

BRIEF DESCRIPTION OF THE INVENTION

Embodiments of the present invention are included to meet these and other needs. One embodiment is an amino-siloxane composition including structure (I):

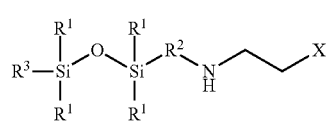

(I)

wherein $R^1$ is independently at each occurrence a $C_1$-$C_5$ aliphatic radical; $R^2$ is a $C_3$-$C_4$ aliphatic radical; $R^3$ is a $C_1$-$C_5$ aliphatic radical or $R^4$, wherein $R^4$ comprises structure (II):

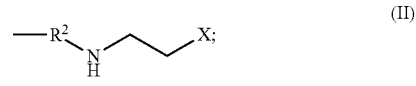

(II)

and X is an electron donating group.

One embodiment is a method of reducing the amount of carbon dioxide in a process stream. The method includes the step of contacting the process stream with a carbon dioxide absorbent composition including an amino-siloxane having structure (I):

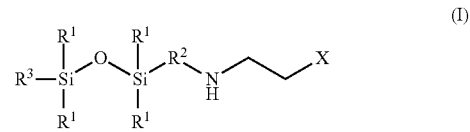

(I)

wherein $R^1$ is independently at each occurrence a $C_1$-$C_5$ aliphatic radical; $R^2$ is a $C_3$-$C_4$ aliphatic radical; $R^3$ is a $C_1$-$C_5$ aliphatic radical or $R^4$, wherein $R^4$ comprises structure (II):

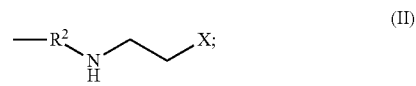

(II)

and X is an electron donating group.

One embodiment is a method of reducing the amount of carbon dioxide in a process stream. The method includes the step of contacting the process stream with a carbon dioxide absorbent composition including an amino-siloxane having structure (Ib):

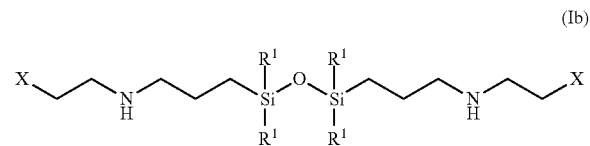

(Ib)

wherein $R^1$ is independently at each occurrence a $C_1$-$C_5$ aliphatic radical; and X includes a $R^5O$— group; a $R^5S$ group; a $(R^5)_2N$— group; or a morpholine group, wherein $R^5$ is independently at each occurrence a $C_1$-$C_5$ aliphatic radical.

DETAILED DESCRIPTION

As discussed in detail below, some of the embodiments of the invention include amino-siloxane compositions and methods of using these compositions as $CO_2$ absorbents. More particularly, the invention relates to amino-siloxane compositions, and methods of using these as $CO_2$ absorbents, such that the amino-siloxanes have low heats of absorption, and further the amino-siloxanes and the related reaction products remain in a substantially liquid state during the $CO_2$ capture process.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the term "aliphatic radical" refers to an organic radical having a valence of at least one consisting of a linear or branched array of carbon and hydrogen atoms, which is not cyclic. By way of example, a $C_1$-$C_5$ aliphatic radical contains at least one but no more than 5 carbon atoms. A methyl group (i.e., $CH_3$—) is an example of a $C_1$ aliphatic radical. Similarly, a butyl group (i.e., $CH_3(CH_2)_3$—) is an example of a $C_4$ aliphatic radical.

As discussed in detail below, some embodiments of the invention are directed to an amino-siloxane composition. In some embodiments, the amino-siloxane composition includes structure (I):

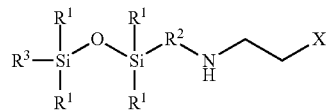
(I)

wherein $R^1$ is independently at each occurrence a $C_1$-$C_5$ aliphatic radical; $R^2$ is a $C_3$-$C_4$ aliphatic radical; $R^3$ is a $C_1$-$C_5$ aliphatic radical or $R^4$, wherein $R^4$ includes structure (II):

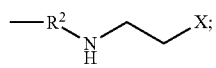
(II)

and X is an electron donating group.

As noted earlier, a $C_1$-$C_5$ aliphatic radical contains at least one but no more than 5 carbon atoms. Similarly, a $C_3$-$C_4$ aliphatic radical contains three or four carbon atoms, and may include a propyl or a butyl radical.

The term "electron donating group" (sometimes also referred to as an electron releasing group) as used herein refers to an atom or a group that releases electrons into a reaction center and stabilizes electron deficient carbocations. Non-limiting examples of suitable electron donating groups include alkoxy groups, hydroxyl groups, sulfide groups, and amine groups.

In some embodiments, X includes a $R^5O$— group; a $R^5S$— group; a $(R^5)_2N$— group; or a morpholine group, wherein $R^5$ is independently at each occurrence a $C_1$-$C_5$ aliphatic radical. In certain embodiments, X includes a $CH_3O$— group; a $C_2H_5O$— group; a $(CH_3)_2N$— group; a $(C_2H_5)_2N$— group, or a morpholine group.

In some embodiments, the amino-siloxane composition is monofunctional, that is, includes a single amine group. In some other embodiments, the amino-siloxane is bifunctional, that is includes two amine groups. In such instances, for example, the amino-siloxane composition may include structure (Ia):

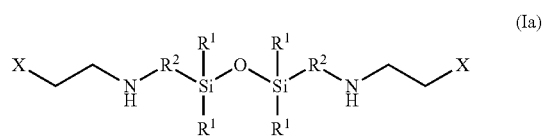
(Ia)

wherein $R^1$ is independently at each occurrence a $C_1$-$C_5$ aliphatic radical; $R^2$ is a $C_3$-$C_4$ aliphatic radical; and X is an electron donating group.

In some embodiments, the amino-siloxane composition includes structure (Ib):

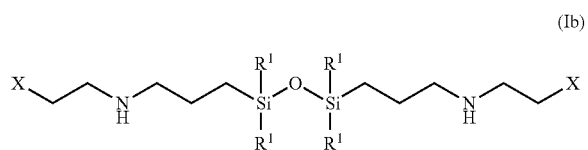
(Ib)

wherein $R^1$ is independently at each occurrence a $C_1$-$C_5$ aliphatic radical; and X is an electron donating group.

In certain embodiments, the amino-siloxane composition includes structure (Ic):

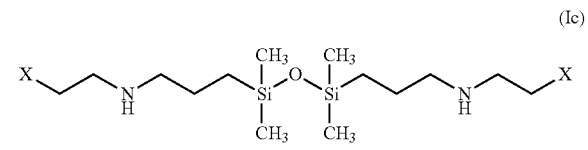
(Ic)

wherein X is an electron donating group. As noted earlier, non-limiting examples of a suitable electron donating group include a $R^5O$— group; a $R^5S$— group; a $(R^5)_2N$— group; or a morpholine group, wherein $R^5$ is independently at each occurrence a $C_1$-$C_5$ aliphatic radical.

A reaction product of the amino-siloxane composition with carbon dioxide ($CO_2$) is also presented. In some embodiments, the amino-siloxane composition having structures (I), (Ia), (Ib), or (Ic) reacts with $CO_2$ to form a reaction product, hereinafter referred to as an adduct. Those skilled in the art will appreciate that a reaction product of a secondary amine with $CO_2$ is a carbamate. As described in detail later, amine-siloxane compositions of the present invention may be useful as $CO_2$ absorbents.

In some embodiments, the present invention provides amino-siloxanes useful as carbon dioxide absorbents, which are substantially liquid under ambient conditions and which remain liquid following exposure to carbon dioxide. For example, in some embodiments, the present invention advantageously provides a liquid amino-siloxane composition, which reacts with $CO_2$ to form an adduct of the amino-siloxane with $CO_2$, the adduct also being substantially liquid under ambient conditions. The term "substantially liquid" as used herein means that the amino-siloxane and the adduct are characterized by a melting temperature or a glass transition temperature lower than the temperature at which the $CO_2$ absorption step is effected.

In certain embodiments, the physical state of the adduct of the amino-siloxane composition with $CO_2$ may be controlled by limiting the degree to which the amino-siloxane composition is reacted with $CO_2$. For example, it may be possible and advantageous to limit the time and conditions of contacting the amino-siloxane composition with $CO_2$ such that the adduct contains less than the theoretical amount of $CO_2$ derived structural units (i.e. carbamate groups). In some embodiments, an amino-siloxane composition, which when fully reacted with $CO_2$ is a solid under ambient conditions, may be maintained in the liquid state when only partially reacted with $CO_2$. In some embodiments, the present invention provides a reaction product of an amino-siloxane composition with $CO_2$ in which less than the theoretical amount of $CO_2$ has reacted with the reactive groups of the amino-siloxane composition.

In some embodiments, the degree of reaction of the amino-siloxane composition with $CO_2$ is in a range from about 10 percent of the theoretical value to about 100 percent of the theoretical value. In other embodiments, the degree of reaction of the amino-siloxane composition with $CO_2$ is in a range from about 20 percent of the theoretical value to about 95 percent of the theoretical value. In some other embodiments, the degree of reaction of the amino-siloxane composition with $CO_2$ is in a range from about 30 percent of the theoretical value to about 90 percent of the theoretical value.

Optionally, the amino-siloxane composition may also include other components, such as, e.g., oxidation inhibitors (to increase the oxidative stability) or anti-foaming agents. The use of oxidation inhibitors, also called antioxidants, may be especially advantageous in those embodiments of the invention wherein the functional groups comprise amine groups. In some embodiments, the amino-siloxane composition may further include a co-solvent or a carrier solvent. However, the amount of co-solvent (if present) may be present in an amount that is sufficiently low, such that the $CO_2$ absorption process is not adversely affected.

In certain embodiments, the amino-siloxane composition that is reacted with $CO_2$ to form a reaction product may be substantially free of a co-solvent. The term "substantially free" as used in this context means that the amino-siloxane composition contains less than about 10 volume percent of co-solvent or a carrier fluid. In some embodiments, the amount of co-solvent or a carrier fluid is less than about 5 volume percent. In some embodiments, the amino-siloxane composition is substantially free of a solvent selected from the group consisting of water, ionic liquids, and combinations thereof.

As alluded to previously, in typical $CO_2$ absorption systems, the absorption process may sometimes result in a sharp increase in the viscosity of the liquid absorbent, which can decrease the mass transfer of $CO_2$ into the sorbent. To avoid this problem, the concentration of the absorbent composition may be maintained at low levels (using carrier solvents), which may greatly reduce absorbing capacity, as compared to the theoretical capacity of the neat absorbent. Moreover, energy consumption in such processes may be high, due in large part to the need for heating and evaporation of carrier solvent (for example, water).

Further, conventional silicon or amine-based absorbents may form solids or very high viscosity oils on reaction with $CO_2$. This can negatively impact mass transfer, so that the absorbent material does not react with as much $CO_2$ as is theoretically possible. Furthermore, materials that form solid $CO_2$ reaction products may not readily fit into existing $CO_2$ capture process schemes. Conventional amino-siloxane-based absorbents may also have a relatively high heat of reaction (for example, 2500-2700 kJ/kg $CO_2$ for primary amino-siloxanes). Use of absorbents with higher heats of reaction may require a higher parasitic energy load during desorption.

Surprisingly, the present inventors have identified amino-siloxane compositions that may not require the use of additional solvents in order to achieve an acceptable viscosity level, and have significantly lower heats of reaction. Further, the amino-siloxane compositions have low volatility, high thermal stability, and have a high net capacity for $CO_2$, and as such, are appropriate for large scale implementation. Thus, the amino-siloxane compositions provided herein are expected to provide improvement when utilized to remove $CO_2$ from process streams, as compared to those currently commercially available and/or utilized for this purpose.

As such, a method of reducing the amount of carbon dioxide in a process stream is also presented. The method includes contacting the process stream with a $CO_2$ absorbent composition comprising an amino-siloxane having structures (I), (Ia), (Ib), or (Ic), as described herein.

The process stream is typically gaseous but may contain solid or liquid components, and may be at a wide range of temperatures and pressures, depending on the application. The process stream may be a process stream from industries, such as chemical industries, cement industries, steel industries, a power plant, and the like. In certain embodiments, the process stream is generated from at least one of a combustion process, a gasification process, a landfill, a furnace, a steam generator, and a boiler.

In some embodiments, the process stream includes a gas mixture emitted as a result of the processing of fuels, such as natural gas, biomass, gasoline, diesel fuel, coal, oil shale, fuel oil, tar sands, and combinations thereof. In some embodiments, the process stream includes a gas mixture emitted from a gas turbine. In some embodiments, the process stream includes syngas generated by gasification or a reforming plant. In some embodiments, the process stream includes a flue gas. In certain embodiments, the process stream includes a gas mixture emitted from a coal or natural gas-fired power plant.

The step of contacting may be effected under suitable conditions (for example, temperature, pressure etc.) in a suitable reaction chamber. Non-limiting examples of suitable reaction chambers may include an absorption tower, a wetted wall tower, a spray tower, a venturi scrubber, or combinations thereof. As noted, earlier, the degree of reaction of the amino-siloxane with $CO_2$ may be controlled by varying the reaction duration and reaction conditions.

The method may further include forming an adduct stream and a $CO_2$-lean gas stream after the step of contacting the process stream with the $CO_2$ absorbent composition. The term "$CO_2$-lean gas stream" as used herein refers to a gas stream having a $CO_2$ content lower than that of the process stream. The adduct stream may be further subjected to one or more desorption steps to release $CO_2$ and regenerate the absorbent composition. The $CO_2$-lean stream may also be further transported to another vessel or system for subsequent processing steps.

In some embodiments, the method of reducing the amount of carbon dioxide in a process stream includes the step of contacting the process stream with a carbon dioxide absorbent composition containing an amino-siloxane having structure (Ib):

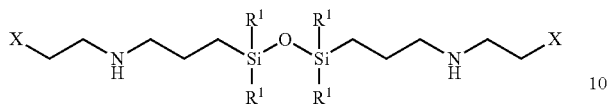

(Ib)

wherein $R^1$ is independently at each occurrence a $C_1$-$C_5$ aliphatic radical; and X comprises a $R^5O$— group; a $R^5S$ group; a $(R^5)_2N$— group; or a morpholine group, wherein $R^5$ is independently at each occurrence a $C_1$-$C_5$ aliphatic radical.

The amino-siloxane compositions and methods of using them, presented herein may benefit from economies of scale which may lower their cost. Further, the amino-siloxane compositions have relatively low viscosity, low heat of reaction, high thermal stability, and may be provided using the synthetic methods disclosed herein. It is believed that the compositions and methods provided by the present invention will be especially useful in power plants requiring absorbents for reducing carbon dioxide emissions.

EXAMPLES

General Synthetic Method for Amino-Siloxanes with Electron Donating Groups

Comparative Examples A-E and Examples A-E

A five-fold molar excess of the starting primary amines were charged to a flask equipped with a magnetic stirbar, addition funnel, and nitrogen inlet. The reaction flask was immersed in a room temperature water bath in order to control any exotherm. 1,3-bis(iodopropyl)-1,1,3,3-tetramethyldisiloxane was then added dropwise over 15-30 minutes. The reaction mixture was then allowed to stir overnight.

At this point, excess amine was stripped off using a rotary evaporator. If the crude bis HI salts were found to be solid, they were purified by recrystallization using mixtures of ethyl acetate and methanol. They were then dried under reduced pressure. The free amines were prepared by mixing the bis HI salts with a 10% NaOH and heptane. After stirring until all the solids had disappeared, the mixtures were transferred to a separatory funnel. The heptane phase was then isolated, washed with water and a saturated sodium chloride solution, and dried over anhydrous sodium sulfate. The heptane was stripped on a rotary evaporator.

If crude bis HI salts were oils, they were converted to the free amines by treatment with 10% NaOH and heptane as described earlier. The crude materials were then purified by distillation. The analytical data for amino-siloxanes compounds synthesized in Comparative Examples A-E and Examples A-E is provided below. Chemical structures for amino-siloxanes compounds synthesized in Comparative Examples A-E and Examples A-E are shown in Structures II and III:

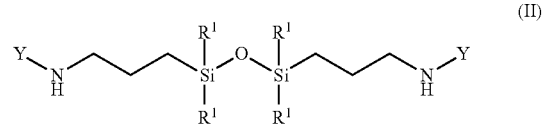

(II)

Comparative Example A

Y=—CH$_3$

Comparative Example B

Y=—C$_2$H$_5$

Comparative Example C

Y=—C$_3$H$_7$

Comparative Example D

Y=—C$_4$H$_9$

Comparative Example E

Y=—(CH$_2$)$_3$—OCH$_3$

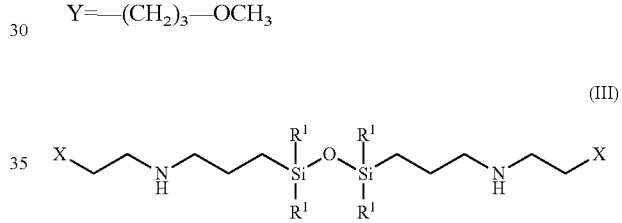

(III)

Example A

X=—OCH$_3$

Example B

X=—OC$_2$H$_5$

Example C

X=—N(CH$_3$)$_2$

Example D

X=—N(C$_2$H$_5$)$_2$

Example E

X=morpholine

Comparative Example A $^1$H NMR (CDCl$_3$) δ: 2.52 (t, J=7.2 Hz, 4H), 2.39 (s, 6H), 1.45 (m, 4H), 1.13 (br s, 2H), 0.47 (m, 4H), 0.01 (s, 12H). $^{13}$C{$^1$H}NMR (CDCl$_3$): 55.23, 36.34, 23.51, 15.70, 0.19 ppm. Exact mass MS: Calculated for $C_{12}H_{33}N_2OSi_2$ (M+H$^+$); 277.2131. Found: 277.2139.

Comparative Example B 1,3-Bis(ethylaminopropyl)-1,1,3,3-tetramethyldisdoxane $^1$H NMR (CDCl$_3$) δ: 2.56 (q, J=7.2 Hz, 4H), 2.50 (t, J=7.0 Hz, 4H), 1.41 (m, 4H), 1.01 (t, J=7.2 Hz, 6H), 0.82 (br s, 2H), 0.41 (m, 4H), −0.05 (s, 12H). $^{13}$C{$^1$H}NMR (CDCl$_3$): 53.10, 44.01, 23.85, 15.83, 15.34, 0.21 ppm. Exact mass MS: Calculated for $C_mH_{37}N_2OSi_2$ (M+H$^+$): 305.24444. Found: 305.24160.

Comparative Example C 1,3-Bis(propylaminopropyl)-1,1,3,3-tetramethyldisdoxane $^1$H NMR (CDCl$_3$) δ: 2.53 (t, J=8.0 Hz, 4H), 1.45 (m, 8H), 0.87 (t, J=6.3 Hz, 6H), 0.48 (m, 4H), 0.02 (s, 12H). $^{13}$C{$^1$H}NMR (CDCl$_3$): 53.28, 51.90, 23.90, 23.32, 15.88, 11.82, 0.29 ppm. Exact mass MS: Calculated for $C_{16}H_{41}N_2OSi_2$ (M+H$^+$): 333.27574. Found: 333.27569.

Comparative Example D 1,3-Bis(butylaminopropyl)-1,1,3,3-tetramethyldisdoxane $^1$H NMR (CDCl$_3$) δ: 2.52 (m, 8H), 1.42 (m, 8H), 1.28 (m, 4H), 0.85 (t, J=7.2 Hz, 6H), 0.43 (m, 4H), −0.02 (s, 12H). $^{13}$C{$^1$H}NMR (CDCl$_3$): 53.31, 49.66, 32.37, 23.85, 20.50, 15.84, 13.99, 0.24 ppm. Exact mass MS: calculated for $C_{18}H_{45}N_2OSi_2$ (M+H$^+$); 361.30704. Found: 361.29968.

Comparative Example E 1,3-Bis(3-methoxypropylaminopropyl)-1,1,3,3-tetramethyldisdoxane Boiling point=125-128° C./0.34 mmHg, $^1$H NMR (CDCl$_3$) δ: 3.37 (t, J=6.3 Hz, 4H), 3.26 (s, 6H), 2.61 (t, J=7.2 Hz, 4H), 2.51 (d, J=7.2 Hz, 4H), 1.69 (quintet, J=6.8 Hz, 4H), 1.42 (m, 4H), 1.07 (br s, 2H), 0.43 (m, 4H), −0.03 (s, 12H). $^{13}$C{$^1$H}NMR (CDCl$_3$): 71.32, 58.54, 53.29, 47.16, 30.12, 23.79, 15.80, 0.25 ppm. Exact mass MS: Calculated for $C_{18}H_{45}N_2O_3Si_2$ (M+H$^+$): 393.2969. Found: 393.2979.

Example A 1,3-Bis(2-methoxyethylaminopropyl)-1,1,3,3-tetramethyldisdoxane $^1$H NMR (CDCl$_3$) δ: 3.47 (t, J=5.2 Hz, 4H), 3.33 (s, 6H), 2.75 (t, J=5.2 Hz, 4H), 2.57 (d, J=7.2 Hz, 4H), 1.47 (m, 4H), 1.35 (br s, 2H), 0.47 (m, 4H), 0.01 (s, 12H). $^{13}$C{$^1$H}NMR (CDCl$_3$): 72.11, 58.74, 53.24, 49.26, 23.81, 15.79, 0.24 ppm. Exact mass MS: Calc'd for $C_{16}H_{41}N_2O_3Si_2$ (M+H$^+$); 365.26557. Found: 365.26204.

Example B 1,3-Bis(2-ethoxyethylaminopropyl)-1,1,3,3-tetramethyldisdoxane

Boiling point=118-122° C./0.62 mmHg, $^1$H NMR (CDCl$_3$) δ: 3.51 (t, J=5.4 Hz, 4H), 3.47 (q, J=7.0 Hz, 4H), 2.74 (t, J=5.6 Hz, 4H), 2.57 (t, J=7.2 Hz, 4H), 1.47 (m, 4H), 1.35 (br s 2H), 1.17 (t, J=7.0 Hz, 6H), 0.47 (m, 4H), 0.01 (s, 12H). $^{13}$C{$^1$H}NMR (CDCl$_3$): 69.98, 66.39, 53.29, 49.42, 23.87, 15.86, 15.15, 0.26. Exact mass MS: Calculated for $C_{18}H_{45}N_2O_3Si_2$ (M+H$^+$); 393.29687. Found: 393.29341.

Example C 1,3-Bis[2-(dimethylamino)ethylaminopropyl]-1,1,3,3-tetramethyldisiloxane Boiling point=122-126° C./0.62 mmHg, $^1$H NMR (CDCl$_3$) δ: 2.63 (t, J=6.2 Hz, 4H), 2.54 (t, J=7.2 Hz, 4H), 2.36 (t, J=6.2 Hz, 4H), 2.17 (s, 12H), 1.45 (m, 4H), 1.29 (br s 2H), 0.45 (m, 4H), −0.01 (s, 12H). $^{13}$C{$^1$H}NMR (CDCl$_3$): 59.32, 53.46, 47.35, 45.57, 23.84, 15.86, 0.26. Exact mass MS: Calculated for $C_{18}H_{47}N_4OSi_2$ (M+H$^+$); 391.32884. Found: 391.31959.

Example D 1,3-Bis[2-(diethylamino)ethylaminopropyl]-1,1,3,3-tetramethyldisiloxane Boiling point=143-145° C./0.56 mmHg, $^1$H NMR (CDCl$_3$) δ: 2.63 (t, J=6.4 Hz, 4H), 2.57 (t, J=7.4 Hz, 4H), 2.50 (m, 12H), 1.47 (m, 4H), 1.32 (br s 2H), 0.98 (t, J=7.0 Hz, 12H), 0.48 (m, 4H), 0.02 (s, 12H). $^{13}$C{$^1$H}NMR (CDCl$_3$): 53.37, 52.75, 47.55, 47.10, 23.79, 15.83, 11.82, 0.24. Exact mass MS: Calculated for $C_{22}H_{55}N_4OSi_2$ (M+H$^+$); 447.39144. Found: 447.39639.

Example E 3,3'-(1,1,3,3-Tetramethyldisiloxane-1,3-diyl)bis(N—(2-morpholinoethyl)propan-1-amine)

Boiling point=177-185° C./0.014 mmHg, $^1$H NMR (CDCl$_3$) δ: 3.68 (t, J=4.6 Hz, 8H), 2.68 (t, J=6.2 Hz, 4H), 2.57 (t, J=7.2 Hz, 4H), 2.47 (t, J=6.1 Hz, 4H), 2.42 (m, 8H), 1.48 (m, 4H), 1.39 (br s, 2H), 0.48 (m, 4H), 0.02 (s, 12H). $^{13}$C{$^1$H}NMR (CDCl$_3$): 67.04, 58.49, 53.78, 53.39, 46.07, 23.83, 15.85, 0.32. Exact mass MS: Calculated for $C_{22}H_{51}N_4O_3Si_2$ (M+H$^+$); 475.34997. Found: 475.34875.

CO$_2$ Uptake Procedure

A 25 mL round bottom flask was equipped with a stir paddle/stir shaft and a gas outlet adapter into which was inserted a small amount of glass wool. This apparatus was then weighed on an analytical balance. The test amine was added and the apparatus was re-weighed so that the weight of sample could be determined. The flask was then immersed in a 40° C. oil-bath, attached to an overhead stirrer, and equipped with a glass pipette aimed slightly above the surface of the liquid through which the CO$_2$ was introduced. The outlet tube was connected to a bubbler filled with silicone oil. The gas stream was produced via sublimation of dry ice and was passed through a drying tube (filled with blue indicating Drierite) prior to entering the reaction flask. Once the test was complete, the CO$_2$ flow was discontinued as was stirring. The sample was then cooled to room temperature and the outside of the flask was washed with isopropanol to remove any silicone oil remaining from the oil bath. After drying the outside of the flask, the sample weight was then re-measured. The percent weight gain was calculated by dividing the difference between the final and initial sample weights by the initial value and then multiplying the result by 100. The percentage of theoretical values was derived by comparing the experimentally determined percent weight gains to those expected based on the molecular weight of the test amine, based on the assumption that two amines are required per molecule of $CO_2$.

Calorimetry Experiments

The heats of absorption of $CO_2$ were measured using an OmniCal ReactMax-Z3-UL Reaction calorimeter. Hasteloy-C reactor vessels (25 mL) supplied by the calorimeter manufacturer were used that can withstand pressures up to 34.5 bar. An additional stainless steel vessel was added adjacent to the calorimeter in order to supply heated $CO_2$ to the reactor vessel. This additional vessel was placed in a heated box fitted with a circulating fan. A Siena Instruments Smart-Trak 2 Model# C100L mass flow controller was installed in-between the reactor vessel and the additional stainless steel $CO_2$ storage vessel to measure the amount of $CO_2$ added to the reactor. This mass flow controller has an integrated totalizer to measure the total flow of a gas over a user-defined time.

Unless otherwise noted, the reactor vessel was filled with ~1.5 grams of material, not including the mass of solvent or other additives, and a magnetic stir bar was added. The exact volume of the sample was calculated using the density of each sample. The reactor was sealed, placed inside the calorimeter, with stirring set to ~500-600 RPM and the temperatures of the calorimeter and the $CO_2$ storage vessel were set to the desired temperature. The $CO_2$ storage vessel was filled with $CO_2$ from the supply tank. The system was then allowed to come to equilibrium for 1-2 hours. When both the heat flow and the calorimeter temperature achieved steady-state, the system was considered to be at equilibrium.

The totalizer on the mass flow controller was reset to zero and the reactor was filled with ~20 SCC of $CO_2$, unless otherwise noted. The value on the mass flow controller totalizer was recorded and the reaction was allowed to proceed for 2 hours. This procedure was repeated until no more $CO_2$ was absorbed-typically 7-13 more times.

For each addition of $CO_2$, the baseline value for the heat flow was established and subtracted from the raw data. The baseline-subtracted heat flow was then integrated over the reaction time to determine the total reaction heat. The total amount of $CO_2$ remaining in the headspace of the reactor was calculated from the pressure, temperature, and headspace volume. The total amount of $CO_2$ absorbed by the sample was calculated by subtracting the $CO_2$ remaining in the headspace at the end of the reaction from the total $CO_2$ that was added, plus the $CO_2$ remaining in the headspace after the previous reaction step. The heat of reaction for each step was then calculated by dividing the total reaction heat by the amount of $CO_2$ absorbed by the sample.

As a reference, the heat of absorption of 30% monoethanol amine (MEA) in water was also measured eight times over the time period the above experiments were run. The average value for 30% MEA was found to be 1825 kJ/kg $CO_2$, with a standard deviation of 83 kJ/kg $CO_2$. The high value measured during this time was 2006 kJ/kg $CO_2$, and the low value was 1714 kJ/kg $CO_2$. Thus, the amino-siloxanes of the present invention generally have heats of absorption similar to this 30% MEA reference solution.

Table 1 shows the $CO_2$ uptake date for amino-siloxanes prepared in Comparative Examples A-E and Examples A-E. Table 2 shows the heat of absorption data based on the calorimetric studies.

TABLE 1

Summary of the $CO_2$ uptake data for Comparative Examples A-E and Examples A-E.

| Example | % Wt Gain | % of Theory | Adduct Form |
|---|---|---|---|
| Comparative Example A | 18.3 | 115 | Viscous Liquid |
| Comparative Example B | 16.5 | 114 | Viscous Liquid Crystals within 2 days |
| Comparative Example C | 14.3 | 108 | Viscous Liquid Crystals within 2 days |
| Comparative Example D | 13.1 | 107 | Viscous Liquid |
| Comparative Example E | 11.7 | 104 | Viscous Liquid |
| Example A | 13.2 | 109 | Flowable Liquid |
| Example B | 12.3 | 110 | Flowable Liquid |
| Example C | 13.4 | 119 | Flowable Liquid |
| Example D | 10.8 | 110 | Flowable Liquid |
| Example E | 10.2 | 110 | Viscous Liquid |

The data in Table 1 shows that the amino-siloxanes functionalized with electron donating groups (Examples A-E) exhibited similar $CO_2$ uptake and produced carbamates (adducts) that were readily flowable liquids, when compared to amino-siloxanes free of electron donating groups (Comparative Examples A-D). Further, amino-siloxanes with electron donating groups bonded to the secondary amine via an ethyl radical (Example A) showed better $CO_2$ uptake and produced adducts that were readily flowable liquids, when compared to amino-siloxanes with electron donating groups bonded to the secondary amine via a propyl radical (Comparative Example E).

TABLE 2

Heat of absorption data for Comparative Examples A-E and Examples A-E.

| Example | Δ H (kJ/kg $CO_2$) |
|---|---|
| Comparative Example A | 2168 |
| Comparative Example B | 2151 |
| Comparative Example C | 2125 |
| Comparative Example D | 2175 |
| Comparative Example E | 2082 |
| Example A | 1821 |
| Example B | 1863 |
| Example C | 1768 |
| Example D | 2046 |
| Example E | 1900 |

The data in Table 2 shows that the amino-siloxanes functionalized with electron donating groups (Examples A-E) have lower heats of absorption when compared to amino-siloxanes free of electron donating groups (Comparative Examples A-D). Further, the amino-siloxane with electron donating groups bonded to the secondary amine via an ethyl radical (Example A) showed lower heat of absorption, when compared to amino-siloxane with electron donating groups bonded to the secondary amine via a propyl radical (Comparative Example E).

The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of:" Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A method of reducing the amount of carbon dioxide in a process stream, comprising the step of contacting the process stream with a carbon dioxide absorbent composition which is substantially free of a co-solvent, said carbon dioxide absorbent composition comprising an amino-siloxane comprising structure (I):

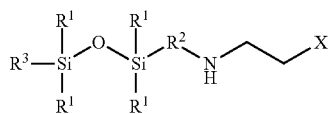

(I)

wherein $R^1$ is independently at each occurrence a $C_1$-$C_5$ aliphatic radical; $R^2$ is a $C_3$-$C_4$ aliphatic radical; $R^3$ is a $C_1$-$C_5$ aliphatic radical or $R^4$, wherein $R^4$ comprises structure (II):

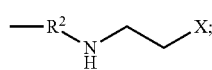

(II)

and X comprises a $R^5O$— group; a $(R^5)_2N$— group; a $R^5S$ group; or a morpholine group, wherein $R^5$ is independently at each occurrence a $C_1$-$C_5$ aliphatic radical.

2. The method according to claim 1, wherein the amino-siloxane comprises structure (Ia):

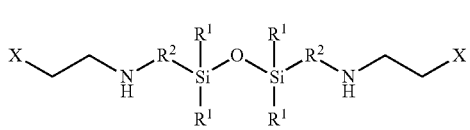

(Ia)

wherein $R^1$ is independently at each occurrence a $C_1$-$C_5$ aliphatic radical; $R^2$ is a $C_3$-$C_4$ aliphatic radical; and X comprises a $R^5O$— group; a $(R^5)_2N$— group; a $R^5S$ group; or a morpholine group, wherein $R^5$ is independently at each occurrence a $C_1$-$C_5$ aliphatic radical.

3. The method according to claim 1, wherein the amino-siloxane comprises structure (Ib):

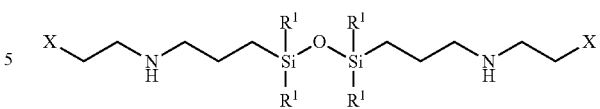

(Ib)

wherein $R^1$ is independently at each occurrence a $C_1$-$C_5$ aliphatic radical; and X comprises a $R^5O$— group; a $(R^5)_2N$— group; a $R^5S$ group; or a morpholine group, wherein $R^5$ is independently at each occurrence a $C_1$-$C_5$ aliphatic radical.

4. The method according to claim 1, wherein the amino-siloxane comprises structure (Ic)

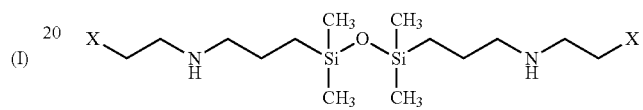

(Ic)

wherein X comprises a $R^5O$— group; a $(R^5)_2N$— group; a $R^5S$ group; or a morpholine group, wherein $R^5$ is independently at each occurrence a $C_1$-$C_5$ aliphatic radical.

5. The method according to claim 1, wherein X comprises a $CH_3O$— group; a $C_2H_5O$— group; a $(CH_3)_2N$— group; a $(C_2H_5)_2N$— group, or a morpholine group.

6. The method according to claim 1, further comprising forming a reaction product of the amino-siloxane with carbon dioxide, wherein the reaction product is substantially liquid at room temperature.

7. The method according to claim1, wherein the process stream comprises syn-gas.

8. A method of reducing the amount of carbon dioxide in a process stream, comprising the step of contacting the process stream with a carbon dioxide absorbent composition which is substantially free of a co-solvent, said carbon dioxide absorbent composition comprising an amino-siloxane having structure (Ib):

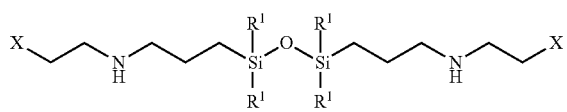

(Ib)

wherein $R^1$ is independently at each occurrence a $C_1$-$C_5$ aliphatic radical; and X comprises a $R^5O$— group; a $R^5S$ group; a $(R^5)_2N$— group; or a morpholine group, wherein $R^5$ is independently at each occurrence a $C_1$-$C_5$ aliphatic radical.

* * * * *